United States Patent [19]

Orton, Jr.

[11] Patent Number: Plant 7,204

[45] Date of Patent: Mar. 27, 1990

[54] DOGWOOD TREE—'GALAXY'

[75] Inventor: Elwin R. Orton, Jr., Somerville, N.J.

[73] Assignee: Rutgers University, New Brunswick, N.J.

[21] Appl. No.: 262,686

[22] Filed: Oct. 26, 1988

[51] Int. Cl.[4] ..... A01H 5/00

[52] U.S. Cl. ..... Plt./51

[58] Field of Search ..... Plt./51

*Primary Examiner*—James R. Feyrer

*Attorney, Agent, or Firm*—Frank B. Robb

[57] ABSTRACT

An interspecific $F_1$ hybrid of the species *Cornus kousa* and *Cornus florida* exhibiting large overlapping white bracts and floriferous in a period from about May 18 to about June 3, the floral display ending about the time plants of *C. kousa* begin their floral display, plants of this cultivar being similar to its seed parent, *C. kousa*, as regards its upright vase shaped habit when youngbut intermediate plants of the two parent species in the nature of the overwintering flower budds, together with freedom from infestation by dogwood borer and "dogwood decline".

2 Drawing Sheets

BACKGROUND OF THE INVENTION

This invention is directed to dogwoods and particularly to a selection of a superior $F_1$ hybrid following interspecific hybridization of an unnamed plant of *Cornus kousa* Hance and an unnamed plant of *Cornus florida* L.

I am not aware of any reported interspecific hybrids of *C. kousa*×*C. florida* and thus I believe the instant hybrid is entirely new to the horticultural world.

Further, my new hybrid as a large-bracted plant exhibits overlapping white bracts and is floriferous from about May 18 to about June 3, the display ending about the time *C. kousa* provides a display of white bracts.

DESCRIPTION OF THE INVENTION

Since this hybrid is the product of an extensive program, and the program has produced a number of other hybrids which also have outstanding characteristics, it is appropriate to compare my new cultivar with others in the program, none of which has been patented up to the present time.

Among the several cultivars which I have selected, the new hybrid hereof is distinguished by identifying the same as 'Rutdan' and as compared with others, this cultivar is upright in habit whereas one, *Cornus*×'Rutfan' is low and spreading in form. 'Rutfan' is similar to one of the others, *Cornus*×'Rutcan' in plant form but differs in having rounded and somewhat overlapping bracts.

'Rutdan' is like another hybrid of this program *Cornus*×'Rutban' in plant form but differs by being less vigorous and the rounded bracts are less broad and the true flowers more exposed in the overwintering buds.

While the bracts of 'Rutdan' do not overlap as much as those of another plant in this program which I identify as 'Rutgan', the floral bracts of the latter are pink as contrasted with the white floral bracts of 'Rutdan'.

It should be stated that I have caused the hybrid 'Rutdan' to be asexually reproduced by budding, grafting or softwood stem cuttings and found the various characteristics noted as well as others not specifically set forth have come true in succeeding generations.

Among those characteristics of my new cultivar, is the freedom from infestation by the dogwood borer and it has not exhibited "dogwood decline" under the growing conditions to which it has been subjected.

Figure 1:
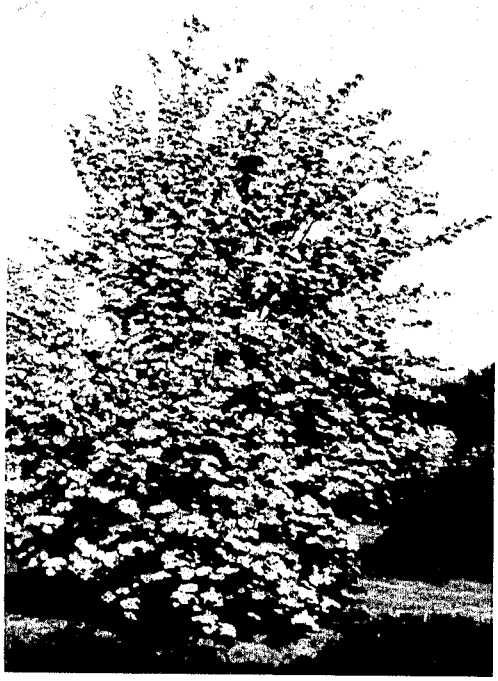
FIG. 1 shows a tree of my new cultivar in bloom.
Figure 2:
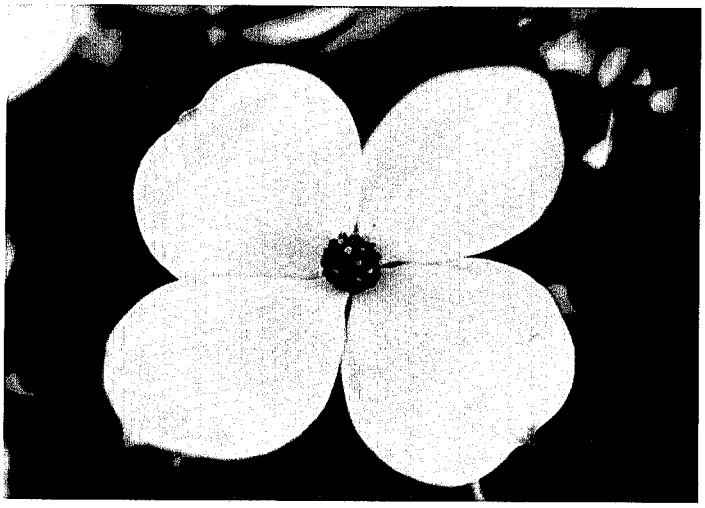
FIG. 2 shows four floral bracts with subtended flower heads typical of my new cultivar.

Other details of the new hybrid 'Galaxy' are set forth in the following detailed description and shown in the drawing which has been produced by photographic process and the colors compared with notations in The Royal Horticulture Colour Chart, where the same may be distinct or helpful in such identification.

Classification:

*Botanic.*—$F_1$ Interspecifichybrid of *C. kousa*×*C. florida.*

Tree: Medium-small, vigorous; upright; dense; somewhat vase-shaped when young; becoming more dense and uniformly spreading with age; hardy; very productive, but highly sterile; regular bearer. The tree disclosed in FIG. 1 of the drawing is about 17 years old, is 5.63 meters tall and has a spread of 4.41 meters.

Trunk: Medium; smooth; when young, but becoming shaggy with age as then exhibitys exfoliating bark.

Branches: Medium; smooth.

*Lenticels.*—Numerous; medium size.

Leaves: Abundant; length 8.9 cm (average=11). width 4.8 cm–8.1 cm (average=6.1 cm). medium; elliptic with acuminate tips; base — cuneate to slightly oblique. Medium thickness. Color-Upper surface-R.H.S. 139A (Green group). Lower surface-R.H.S. 138B (Green group). Margin— entire. Petiole — short — 10–23 mm (Average=16.2). medium thickness.

Flower buds: The tree flowers are small and numerous and are borne in flower heads. Approximately 10–35% of the true flowers are naked or visible, in the overwintering flower buds, as the floral bracts do not completely enclose the true flowers overwinter.

Floral bracts:

*Color.*—Start of floral display — Upper surface is 154 C and lower surface is 154D, both yellow-green group. Midseason floral display — Upper surface is 150D and lower surface is 150D, both yellow-green group. Peak of floral display —

Upper surface is 157A and lower surface is 157B, both Green-white group.

*Size.*—Intermediate in size to those of typical plants of *C. kousa* and *C. florida.* When the floral bracts are fully expanded, the diameter of the inflorescence from tip to tip of the opposing inner bracts is about 116 mm; the diameter of the inflorescence as measured from tip to tip of the opposing outer bracts is about 100 mm.

The average length of the inner bracts is approximately 57.4 mm; the average length of the outer bracts is approximately 48.5 mm.

The shape of the bracts is described as sessile, nearly rounded to obovate with short, acute tip and base broadly tapering to the point of attachment. The margins of adjacent bracts in the involucre often touch or very tightly overlap. The inner bracts are longer and narrower than the outer or lower, bracts.

The average width of the inner bracts at their widest point is 41.3 mm; the average width of the outer bracts at their widest point is 49.9 mm.

Bract length and width will vary from year to year but the inner bracts will usually be longer and narrower than the outer bracts each year.

Peduncle length; Each flower head is borne on a peduncle, the average length being about 4.8 cm. at the time of flowering; whereas those of the *C. kousa* parent average about 7.3 cm in length and those of the *C. florida* parent average about 2.0 cm at the time of flowering.

While absolute peduncle length varies from year to year, the relative peduncle length among the two parents and the hybrid should remain consistent.

Tree:

*Flowers.*—Anthesis of the tiny, relatively inconspicuous true flowers generally commences a few days following the onset of the ornamental display of the large floral bracts. The average number of true flowers per flower head (40.5) in this new hybrid is intermediate to that for the *C. kousa* parent (average=49) and that for the *C. florida* parent (average — 34.5).

Period of floral display (floral bracts) is intermediate to that of plants of the parent species; i.e., occurs in mid-May, commencing about one to two days after completion of the floral display (floral bracts) of most plants of *C. florida* and ending about the time the floral display of most plants of *C. kousa* begins.

*Fruit.*—Fully developed fruit have not been observed, as plants of this new $F_1$ interspecific hybrid are highly sterile. However, some flower heads persist throughout the growing season and, occasionally, the fleshy portion of small parthenocarpic (seedless) fruit will develop, albeit incompletely. However, there is no formation of a syncarp as in *C. kousa,* as the flowers in this new hybrid are distinct and separate in the flower head, or on the receptacle.

Resistance to:

*Insects.*—Good. In field plantings with *C. kousa* and *C. kousa,* the Dogwood Borer has ravaged the plants of *C. florida,* but has not infested plants of my new $F_1$ interspecific hybrid.

*Disease resistance.*—Good. In field plantings with *C. florida* and *C. kousa,* my new $F_1$ interspecific hybrid has been free of the "dogwood decline" that has decimated cultivated and wild stands of *C. florida* in recent years.

I claim:

1. A new and distinct cultivar of dogwood tree, substantially as herein shown and described, characterized particularly as to novelty by the unique combination of its vigor and highly floriferous, small, flowering form and similar to its seed parent *C. kousa* as to its upright, vase-shaped habit when young but intermediate to plants of both parent species *C. kousa* and *C. florida* in the intermediate nature of the overwintering flower buds and the period of floral display, resistance to infestation by dogwood borer and does not exhibit "dogwood decline".

* * * * *

UNITED STATES PATENT AND TRADEMARK OFFICE

CERTIFICATE OF CORRECTION

PATENT NO. : Plant 7,204

DATED : Mar. 27, 1990

INVENTOR(S) : Elwin R. Orton, Jr.

It is certified that error appears in the above-identified patent and that said Letters Patent is hereby corrected as shown below:

Title page, item [54], change the title to read --DOGWOOD TREE- 'RUTDAN'--.

Column 2, line 7, change "'Galaxy'" to read --'Rutdan'--.

Signed and Sealed this

Twenty-fifth Day of August, 1992

*Attest:*

*Attesting Officer*

DOUGLAS B. COMER

*Acting Commissioner of Patents and Trademarks*